(12) United States Patent
Okuda et al.

(10) Patent No.: US 11,963,567 B2
(45) Date of Patent: Apr. 23, 2024

(54) COSMETIC TREATMENT METHOD AND ASSEMBLY

(71) Applicant: L'OREAL, Paris (FR)

(72) Inventors: Shinsuke Okuda, Kawasaki (JP);
Makoto Kawamoto, Kawasaki (JP);
Henri Samain, Chevilly Larue (FR);
Jean-Baptiste Blanc, Chevilly Larue (FR); Alexis Leonard, Chevilly Larue (FR); Franck Giron, Chevilly Larue (FR); Caroline Lebre, Chevilly Larue (FR); Anne Bouchara, Chevilly Larue (FR)

(73) Assignee: L'OREAL, Paris (FR)

( * ) Notice: Subject to any disclaimer, the term of this patent is extended or adjusted under 35 U.S.C. 154(b) by 177 days.

(21) Appl. No.: 16/626,741

(22) PCT Filed: Jun. 30, 2017

(86) PCT No.: PCT/JP2017/025061
§ 371 (c)(1),
(2) Date: Dec. 26, 2019

(87) PCT Pub. No.: WO2019/003453
PCT Pub. Date: Jan. 3, 2019

(65) Prior Publication Data
US 2020/0128897 A1    Apr. 30, 2020

(51) Int. Cl.
*A41G 5/00*    (2006.01)
*A41G 5/02*    (2006.01)
(Continued)

(52) U.S. Cl.
CPC ............ *A41G 5/02* (2013.01); *A61Q 1/10* (2013.01); *A45D 2/48* (2013.01);
(Continued)

(58) Field of Classification Search
CPC .. A45D 2200/25; A45D 40/26; A45D 40/262; A45D 40/265; A45D 2/48; A46B 2200/106; A41G 5/02
See application file for complete search history.

(56) References Cited

U.S. PATENT DOCUMENTS 3,935,872 A    2/1976  Aylott
4,018,336 A    4/1977  Aylott
(Continued)

FOREIGN PATENT DOCUMENTS

FR    2 968 520 A1    6/2012
JP    2009-291344 A    12/2009
(Continued)

OTHER PUBLICATIONS

International Search report dated Mar. 23, 2018 in PCT/JP2017/025061 filed Jun. 30, 2017.
(Continued)

*Primary Examiner* — Rachel R Steitz
(74) *Attorney, Agent, or Firm* — Oblon, McClelland, Maier & Neustadt, L.L.P.

(57) ABSTRACT

Cosmetic treatment method for adding fibers to natural eyelashes, comprising: a) applying an adhesive composition (A) to at least part of the eyelashes, b) bringing fibers (12) borne by an applicator (10) into contact with said adhesive composition (A) present on said eyelashes, c) moving the applicator (10) away from the eyelashes, so as to release fibers (12) which adhere to said eyelashes.

17 Claims, 4 Drawing Sheets

(51) Int. Cl.
*A61Q 1/10* (2006.01)
*A45D 2/48* (2006.01)
*A61K 8/81* (2006.01)

(52) U.S. Cl.
CPC ....... *A46B 2200/106* (2013.01); *A61K 8/8111* (2013.01); *A61K 2800/87* (2013.01)

(56) References Cited

U.S. PATENT DOCUMENTS

| | | | |
|---|---|---|---|
| 4,135,527 A * | 1/1979 | Montiel | A45D 34/045 132/200 |
| 8,424,542 B1 | 4/2013 | Han | |
| 9,215,901 B1 | 12/2015 | Schroeder | |
| 9,833,028 B2 * | 12/2017 | Jang | A45D 2/48 |
| 2004/0134507 A1 * | 7/2004 | Gueret | A46B 9/021 132/218 |
| 2013/0213427 A1 * | 8/2013 | Dinh | A41G 5/02 132/201 |
| 2015/0216246 A1 | 8/2015 | Ahn et al. | |
| 2016/0058088 A1 * | 3/2016 | Le | A41G 5/02 132/201 |
| 2016/0264334 A1 | 9/2016 | Han et al. | |
| 2017/0027844 A1 | 2/2017 | Okura et al. | |

FOREIGN PATENT DOCUMENTS

| | | |
|---|---|---|
| JP | 2017-513837 A | 6/2017 |
| JP | 2018-31100 A | 3/2018 |
| KR | 10-1342686 B1 | 1/2014 |
| WO | WO 2004/055081 A2 | 7/2004 |
| WO | WO 2014/110145 A1 | 7/2014 |
| WO | WO 2015/091513 A1 | 6/2015 |
| WO | WO 2015/116247 A1 | 8/2015 |
| WO | WO 2016/153773 A1 | 9/2016 |
| WO | WO 2016/164001 A1 | 10/2016 |
| WO | WO 2017/021240 A1 | 2/2017 |

OTHER PUBLICATIONS

Japanese Office Action dated Feb. 1, 2021 in Japanese Patent Application No. 2019-572236 (with English translation), 6 pages.

* cited by examiner

COSMETIC TREATMENT METHOD AND ASSEMBLY

TECHNICAL FIELD

Field of the Invention

The present invention relates to cosmetic treatment methods for adding fibers to natural eyelashes and corresponding assemblies.

BACKGROUND ART

Prior Art and Objectives of the Invention

Eyelash extensions and false eyelashes are used for enhancing the length, thickness and fullness of natural eyelashes.

Several methods of applying eyelash extensions may be carried out. The main method is individually adhering the fibers forming the extensions to the lash line one-by-one, thereby preventing the fibers from sticking to one another. Eyelash extensions may remain on for approximately three to four weeks.

False eyelashes are generally designed to be worn for a shorter period of one or two days. They are generally presented as a strip of fibers. For applying the false eyelashes, the strip is glued on the roots of the eyelashes, after applying a glue either on the base of the strip or directly on the roots of the eyelashes.

The application of eyelash extensions needs to be made by a professional, is quite expensive and takes usually one to two hours.

Another disadvantage of the eyelash extensions or false eyelashes is that they are not sterile, which can lead to infections.

US2016/0264334 provides a packaging for at least one false eyelash in which contact with the false eyelashes is minimized to maintain the quality, appearance and integrity of the false eyelashes.

DISCLOSURE OF INVENTION

There is a need to benefit from a method for the cosmetic treatment of eyelashes by adding supplemental fibers to natural eyelashes that can be carried out rapidly, easily and on oneself if possible.

[Cosmetic Treatment Method]

The present invention aims to meet this need and achieves this by a cosmetic treatment method for adding fibers to natural eyelashes, comprising:
 a) applying an adhesive composition to at least part of the eyelashes,
 b) bringing fibers borne by an applicator into contact with said adhesive composition present on said eyelashes,
 c) moving the applicator away from the eyelashes, so as to release fibers which adhere to said eyelashes.

The method according to the invention makes it possible to create an eyelash extension effect with a beautiful alignment of eyelashes and fibers. The method may be implemented in an institute or at home. Numerous fibers may be applied on eyelashes in an easy gesture, in a time being less than for example 10 min, if not less than 1 min.

In the present invention, "natural eyelashes" and "eyelashes" are both used to name the natural eyelashes.

An "adhesive" composition denotes any material capable of withstanding being torn off, with or without a long-lasting adhesive strength.

The fibers are retained on the applicator in step b), the fibers being releasable.

The density of the fibers added to the eyelashes may be adjusted for example by providing the applicator with a greater or lesser density of fibers, thus impacting the density of fibers after transfer to the eyelashes. The density of fibers on the applicator may be between 10 and 40000 fibers/cm$^2$ and more preferably between 20 and 20000 fibers/cm$^2$, more preferably between 50 and 10000 fibers/cm$^2$, still more preferably between 75 and 1000 fibers/cm$^2$, in particular between 100 and 500 fibers/cm$^2$, for example between 150 and 300 fibers/cm$^2$, like about 200 fibers/cm$^2$. This density is not necessary uniform and may vary. The space between two adjacent fibers on the applicator, which is also called "mean-distance", measured at the root of the fibers, is preferably between 10 and 250 each fiber having preferably, in this measurement, a round shape, the measured distance being the littlest distance and the mean-distance being calculated as the mean of all distances.

The adhesive composition may be applied in step a) to said at least part of the eyelashes in a continuous or discontinuous manner. The adhesive composition may be applied in step a) on the eyelashes, preferably from the roots of the eyelashes, over a length of the eyelashes ranging from about 0.1 mm to about 10 mm, better 0.5 mm to 10 mm, still better 1 mm to 5 mm. The length of fibers on which the adhesive composition is applied in step a) may be 100% (of the natural length of the eyelashes), better in a range of 1 to 70% of the natural length of the eyelashes, still better in a range of 5 to 30% of the natural length of the eyelashes. Some of the eyelashes may not be covered by the adhesive composition. The length of the eyelashes covered by the adhesive composition may not be identical for all the eyelashes.

Step b) may be carried out by bringing fibers into contact with the eyelashes, the fibers being substantially parallel to the eyelashes. Step b) may be carried out by bringing fibers into contact with the top or lower part of the upper fringe of eyelashes. Step b) is preferably carried out by bringing fibers into contact with the same part of the upper fringe of eyelashes, which was treated by the adhesive composition. This means that if the adhesive composition is applied on the top part of the upper fringe, the fibers are also preferably brought into contact with the top part of the upper fringe. If the adhesive composition is applied on the lower part of the upper fringe, the fibers are also preferably brought into contact with the lower part of the upper fringe. In a preferred embodiment, step b) is carried out by bringing fibers into contact with the top part of the upper fringe of eyelashes.

The applicator may be brought close to the eyelashes in a tangential movement until the fibers contact the adhesive composition. This "tangential movement" may also be qualified as a "grazing movement".

The holding force for holding the fibers on the applicator is advantageously lower than the adhesive force for adhesion of the fibers to the adhesive composition present on said eyelashes.

The adhesive force for adhesion of the fibers to the adhesive composition is preferably at least double the holding force for holding the fibers on the applicator. This makes it possible to guarantee that the fibers detach properly from the applicator. The force to be exerted on the fibers in order to release them from the applicator may be less than or equal to 15 mN.

The fibers advantageously present a first end portion, also called root or root portion, and a second end portion, the fibers being borne by the applicator by the first end portion, the second end portion being a free end portion.

[Assembly]

The present invention also relates to an assembly for the cosmetic treatment of adding fibers to natural eyelashes, in particular for the implementation of the method as defined above, comprising:

an adhesive composition to be applied to the eyelashes,
an applicator retaining releasable fibers, the applicator making it possible to bring the fibers into contact with the adhesive composition applied to the eyelashes to enable them to adhere to said composition and to release fibers.

In the method and/or in the assembly according to the invention, the fibers may be positioned in various ways on the applicator, depending on the desired result. The fibers are for example arranged as a bundle of fibers on the applicator. The fibers may be substantially parallel to one another on the applicator. The fibers may be arranged on the applicator in a shape of at least part of a bow of false eyelashes. The roots of the fibers may, on the applicator, follow a curve that is either in a plane or out of any plane.

The fibers may be oriented perpendicular to the support surface of the applicator or make an angle with the normal to this surface, in particular an angle ranging up to 45°.

The fibers, when borne by the applicator, may not be linked to one another other than via the applicator. In such case, the fibers are individual isolated fibers. They may not be organized on a strip nor in tufts.

The fibers may be retained on the applicator by bonding or friction or by a mechanical system comprising one or more parts that can be moved relative to one another, the latter being able to pass from a fiber-retaining configuration to a fiber-releasing configuration, the force to be exerted on these fibers in order to release them from the applicator being greater in the retaining configuration than in the releasing configuration. The mechanical system comprises for example a spring that grips the fibers between its coils, in the retaining configuration, the spring being able to be stretched in order to open the coils and release the fibers. The fibers may be retained between the coils of the spring, the fibers being substantially perpendicular to the longitudinal axis of the spring. The spring may be operated manually between the retaining and the releasing configurations. The spring may comprise ends attached to actuating levers that are operated manually. Alternatively, the spring is compressed or released along its longitudinal axis which is the longitudinal axis of the applicator, the applicator having for example a push button and two abutments near both ends of the spring, one abutment being preferably movable along the longitudinal axis when actuating the push button, the other abutment being preferably immobile.

The fibers may be retained on the applicator by at least one material, the mechanical strength of which is degraded by a stimulus, the method comprising subjecting the applicator to said stimulus so as to reduce the force to be exerted on the fibers in order to release them from the applicator, the exposure to the stimulus taking place before and/or during the contact of the fibers with the adhesive composition present on the eyelashes. This solution is particularly advantageous since it enables the user to use the system without precautions while obtaining the desired make up result. A second advantage lies in the field of the production up to the delivery. The stimulus is for example thermal, said material then preferably comprising a wax, in particular beeswax, candelilla wax or paraffin wax. As a variant, the stimulus is chemical and comprises the exposure of the applicator to a solvent of said material, preferably water.

The fibers may be placed on the applicator by an electrostatic flocking method or may be positioned by a mechanical system.

The fibers may detach completely from the applicator during the implementation of the method. As a variant, the fibers may comprise a base at the first end portion that remains trapped by the applicator and a releasable portion that is released. In this case, the fibers may comprise a predefined area that is mechanically weakened or sensitive to a stimulus that makes it possible to mechanically weaken it, in particular a thermal or chemical stimulus, the force to be exerted in order to give rise to the separation of the releasable portion from the root being lower than the adhesive force for adhesion of the releasable portion to the adhesive composition. The predefined area may be located at the same location on the length of the fiber for all the fibers. As a variant, this is not the case, which makes it possible, after release, to have fibers of variable length, which may impart different aesthetic effects on the eyelashes.

The fibers may be retained on the applicator by a multiple holding system, including a first holding system that releases the fibers for an exerted force lower than the adhesive force for adhesion of the fibers to the adhesive composition, and a second holding system that ensures, when combined with the first, the retention of the fibers up to a force greater than the adhesive force for adhesion of the fibers to the adhesive composition, the second system being modified during the use of the applicator for applying the fibers to the adhesive composition so as to bring the force to be exerted in order to give rise to the release of the fibers to a value lower than the adhesive force for adhesion of the fibers to the adhesive composition. The modification may comprise the exposure of the second holding system to a thermal or chemical stimulus.

The invention also relates to an applicator for an assembly as defined above, retaining releasable fibers that detach from the applicator when a tensile force equal to 15 mN, or even equal to 20 mN, is exerted on it.

[Fibers]

The term "fiber" should be understood according to the invention as meaning an object of length L and of diameter D such that L is greater than D and preferably very much greater than D, D being the diameter of the circle in which the cross section of the fiber is inscribed. In particular, the ratio L/D (or aspect ratio) is chosen in the range from 3.5 to 2500, preferably from 10 to 1000 and better still from 20 to 500.

The fibers that can be used in the invention may be fibers of synthetic or natural, and mineral or organic, origin. They may be short or long, individual or organized, for example braided, and hollow or solid. They may have any shape, for example curved or straight. They may especially have a circular or polygonal (square, hexagonal or octagonal) cross section. In particular, their ends may be blunted and/or smoothed to prevent injury.

In particular, the fibers may have a length ranging from 0.5 mm to 20 mm.

Their cross section may range from 20 to 150 µm, 30 to 120 µm, even better still from 40 to 120 µm.

The weight or yarn count of the fibers is often given in denier or decitex and represents the weight in grams per 9 km of yarn. The fibers according to the invention have for example a yarn count chosen in the range from 0.1 to 100 denier, preferably from 1 to 70 denier and better still from 5 to 60 denier.

The fibers may be those used in the manufacture of textiles, and especially silk fibers, cotton fibers, wool fibers, flax fibers, cellulose fibers—especially extracted in particular from wood, from vegetables or from algae, rayon fibers, polyamide (Nylon®) fibers, viscose fibers, acetate fibers, especially rayon acetate fibers, acrylic polymer fibers, especially polymethyl methacrylate fibers or poly(2-hydroxyethyl methacrylate) fibers, polyolefin fibers and especially polyethylene or polypropylene fibers, polyethylene terephthalate (PET) fibers, polybutylene terephthalate (PBT) fibers, glass fibers, silica fibers, carbon fibers, especially fibers of carbon in graphite form, polytetrafluoroethylene (such as Teflon®) fibers, insoluble collagen fibers, polyester fibers, polyvinyl chloride fibers or polyvinylidene chloride fibers, polyvinyl alcohol fibers, polyacrylonitrile fibers, chitosan fibers, polyurethane fibers, polyethylene phthalate fibers, or fibers formed from a mixture of polymers such as those mentioned above, for instance polyamide/polyester fibers.

The fibers may be human hair.

Furthermore, the fibers may be optionally surface-treated, optionally coated with a protective layer or a layer intended to give them a color.

Use may be made of flame-retardant acrylic fibers of "Kanekalon" brand.

The fibers are for example those sold under the reference Minke-props SKINTEX Flock ref. 590502.

It is possible to use identical fibers or as a variant a mixture of fibers that differ from one another in length, cross section, material, shape and/or cross section. The use of fibers of various lengths may impart greater naturalness. So may a mixture of colors. In a particular embodiment, the applicator of the assembly retains a mixture of fibers that differ from one another in color. The colors of fibers may be mixed in an organized manner or randomly. Different colors or associations of colors in the fibers can be implemented, without departing from the scope of the invention. Fibers producing special effects, such as transparent fibers, shiny fibers, may also be included. This can create new aesthetic effects on the eyelashes.

[Adhesive Composition]

The adhesive composition according to the invention is suitable for application to the eyelashes and eyelid, and for cosmetic use.

The adhesive composition comprises or is constituted of an adhesive material.

For the purposes of the present invention, the term "material" means a polymer or a polymeric system that may comprise one or more polymers of different natures. This adhesive material may be in the form of a polymer solution or a dispersion of polymer particles in a solvent. This adhesive material may in addition contain a plasticizer. This adhesive material must have a certain tackiness defined by its viscoelastic properties.

The adhesive materials according to the invention may for example be chosen among pressure sensitive adhesives, for instance those cited in the "Handbook of Pressure Sensitive Adhesive Technology" $3^{rd}$ edition, D. Satas.

The adhesive material may be chosen among acrylic polymers or copolymers.

The pressure-sensitive adhesive materials may be chosen from acrylic polymers, especially copolymers of acrylate and methacrylate, pressure-sensitive adhesives based on rubber or based on styrene copolymers, for example such as styrene-isoprene-styrene (SIS) and styrene-butadiene-styrene (SBS) copolymers.

They may also be urethane polymers, polyurethanes, silicones, such as Bio-PSAs, ethylene/vinyl acetate polymers, block copolymers based on styrene or natural rubbers, chloroprene, butadiene, isoprene, neoprene or the like.

As nonlimiting examples of pressure-sensitive adhesives based on rubbery polymers, mention may in particular be made of natural rubber (poly(cis-1,4-isoprene)), methyl methacrylate-isoprene graft copolymers, styrene-butadiene copolymers, butyl rubber, acrylonitrile-butadiene rubber, styrene-isoprene block copolymers, polybutadiene, ethylene-butylene block copolymers and polychloroprene.

Among the pressure-sensitive adhesives comprising polar acrylic polymers, mention may be made of block or statistical copolymers based on acrylic acid, alkyl acrylates and alkyl methacrylates, and also the copolymers of these acrylics with ethylene and vinyl acetate.

Examples of acrylic copolymers that may be suitable are available commercially under the brands EASTAREZ 2010, 2020 and 2050 (Eastman Chemical Co.), ACRONAL V210 (BASF), MOWILITH LDM 7255, REVACRYL 491 (Clariant) and FLEXBOND 165 (Air Products). As a preferred example of acrylic copolymers may be cited the use of acrylates/ethylhexyl acrylate copolymer commercialized by DAITO KASEI KOGYO under the name Daitosol 5500GM.

The adhesive composition may for example be chosen among the adhesive composition for eyelashes called DUO®, commercialized by American International Industries, and the Daitosol 5500 GM from DAITO KASEI KOGYO.

Commercial examples of polymeric rubbers that may be suitable are known under the brands RICON 130 polybutadiene (Atofina Sartomer) and ISOLENE 40 polyisoprene (Elementis).

Examples of polyurethane-based adhesives that may be suitable are available under the brands SANCURE 2104 (Novéon) and VYLON UR 1400 (Toyobo Vylon).

Examples of vinyl acetate copolymers that may be suitable are available commercially under the brands PVP/VA 6-630 (International Specialty Products) and FLEXBOND 149 (Air Products).

Examples of vinyl alcohol/vinyl acetate copolymers are available commercially under the brands CELVOL 107 (Celanese) and ELVANOL 50-42 (DuPont).

Mention may also be made of the block or statistical copolymers comprising at least one monomer or a combination of monomers whose resulting polymer has a glass transition temperature lower than ambient temperature (25° C.), these monomers or combinations of monomers possibly being chosen from butadiene, ethylene, propylene, isoprene, isobutylene, a silicone, and mixtures thereof. Examples of such materials are block polymers of the styrene-butadiene-styrene, styrene-(ethylene-butylene)-styrene or styrene-isoprene-styrene type, for instance those sold under the trade names "Kraton" from Kraton or "Vector" from Dexco Polymers.

The adhesive materials according to the invention may also comprise tackifying resins, such as rosins or rosin derivatives such as hydrogenated rosins, rosin esters, hydrogenated rosin esters, terpenes, aliphatic or aromatic hydrocarbon-based resins, phenolic resins, styrene resins and coumarone-indene resins. Mention will also be made of the compounds such as shellac, sandarac gum, dammar resins, elemi gum, copal resins, benzoin, and gum mastic.

Mention may also be made of silicone resins, which are crosslinked polyorganosiloxane polymers.

The nomenclature of silicone resins is known under the name "MDTQ", the resin being described as a function of the various siloxane monomer units it comprises, each of the letters M, D, T and Q characterizing a type of unit.

Among these resins, mention may in particular be made of the siloxysilicate resins, which may be trimethyl siloxysilicates of formula $[(CH_3)_3XSiXO]_xX(SiO_{4/2})_y$ (MQ units) in which x and y are integers ranging from 50 to 80, the lipodispersible film-forming polymers in the form of non-aqueous dispersions of polymer particles, also known as NADs Use may be made, as non-aqueous dispersion of hydrophobic film-forming polymer, of dispersions of particles of a grafted ethylenic polymer, preferably an acrylic polymer, in a liquid oily phase for example, in the form of surface-stabilized particles dispersed in the liquid fatty phase.

The dispersion of surface-stabilized polymer particles can be manufactured as described in the document WO 04/055081.

Mention may also be made of dispersions of $C_1$-$C_4$ alkyl (meth)acrylate polymer particles; stabilized by a stabilizing agent chosen from isobornyl (meth)acrylate polymers, as described in document WO 2015/091513.

Use may also be made of UV-reactive adhesives.

In examples, use is made of the Pros-Aide (acrylic latex) Cream Blend 331 Adhesive, or the AQ1350 Eastman Chemical (sulfopolyester soluble polymer) adhesive.

[Application of the Adhesive Composition]

The adhesive composition can be applied as a continuous film on the eyelashes, especially when the density of the fibers on applicator is not too high.

As a variant, the adhesive composition is applied by making non-adhesive areas between the adhesive areas, which offers control over the density and the distribution of the fibers that remain attached to the eyelashes.

Use may be made of an applicator that transfers the adhesive composition. In particular, the assembly according to the invention may comprise an adhesive applicator for applying the adhesive composition to the eyelashes. In such case, the adhesive applicator comprises for example a flocked end piece. The adhesive applicator may have the shape to conform to the shape of lashes roots. In this particular case, the gesture is simple since one just has to approach the adhesive applicator close to the lash fringe and then allow the contact to make the adhesive deposit on the root of the lashes. The adhesive applicator may also comprise for example a pen distributing the adhesive composition or an applicator cooperating with a container housing the adhesive composition, for example an applicator provided with a thin brush or with a flocked thermoplastic tip.

BRIEF DESCRIPTION OF DRAWINGS

Brief Description of the Figures

The invention may be better understood from reading the following detailed description of non-limiting exemplary embodiments thereof and from examining the appended drawing, in which.

BEST MODE FOR CARRYING OUT THE INVENTION

Detailed Description of Embodiments

Figure 2:
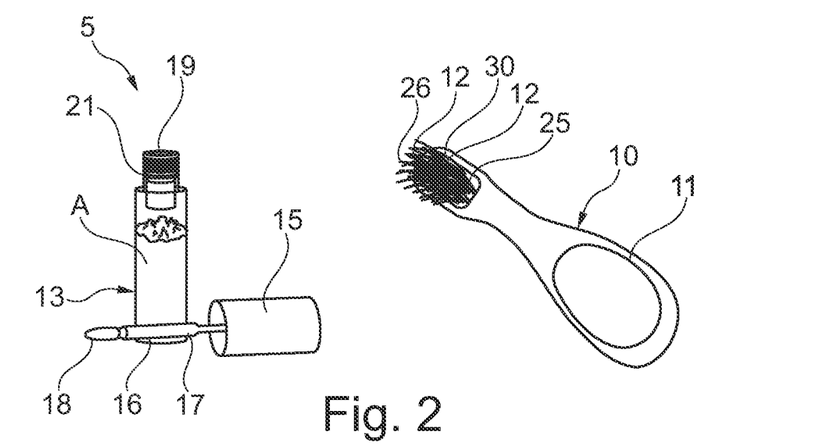
FIG. 2 represents schematically and in perspective an example of a cosmetic assembly according to the invention.

The method according to the invention is implemented with the aid of an assembly 5 (also called "kit") according to the invention, shown in FIG. 2.

The assembly 5 comprises an adhesive composition A contained in a container 13 and an applicator 10 that comprises a gripping portion 11 and fibers 12 which are held on the applicator 10 at a first end portion 25.

The adhesive composition A may for example be chosen among the adhesive composition for eyelashes called DUO®, commercialized by American International Industries, or the one called Daitosol 5500GM, an acrylates/ethylhexyl acrylate copolymer commercialized by DAITO KASEI KOGYO. Another convenient adhesive composition may also be used.

The container 13 comprises a threaded neck 21 and a cap 15 for closing the container by cooperating with the threaded neck 21, the cap 15 supporting an adhesive applicator 16. The adhesive applicator 16 comprises a shaft 17 and an application element 18 at a free end. A wiping element 19 fits, in this example, to the interior side of the neck 21. The application element 18 may be a flocked support. It is loaded with the adhesive composition A in the container 13 before passing through the wiping element 19 for being used in the first step 1 of the method.

The applicator 10 comprises the gripping portion 11, which may have other shapes than represented. The fibers 12 have the first end 25, or root, bonded to the applicator 10 on a support surface 30 thereof and a second free end 26.

A layer of an elastomer, for example the elastomer known as the SILFLO, commercialized by MONADERM under reference GOSILFLO), with a thickness of 0.050 mm, is spread out on a support of application. Before elastomer's reticulation, fibers are flocked on the support thanks to an electrostatic flocking process, materialized by a manual flocking device as the Microflocker from Campbell Coutts LTD Company. Fibers are caught in the elastomer by friction.

As shown in FIG. 2, the fibers 12 are not linked to one another other than via the applicator 10. They are individually isolated. It is possible to use fibers of the same nature, diameter, length, shape or color, or fibers of different nature, length, diameter, shape and/or color for a same eyelash. The shape of the support surface 30 is a plane or not. In the present embodiment, the fibers 12 are locally oriented perpendicularly to the support surface 30 that bears them.

The density of fibers is around 200 fibers/cm$^2$.

Figure 5:
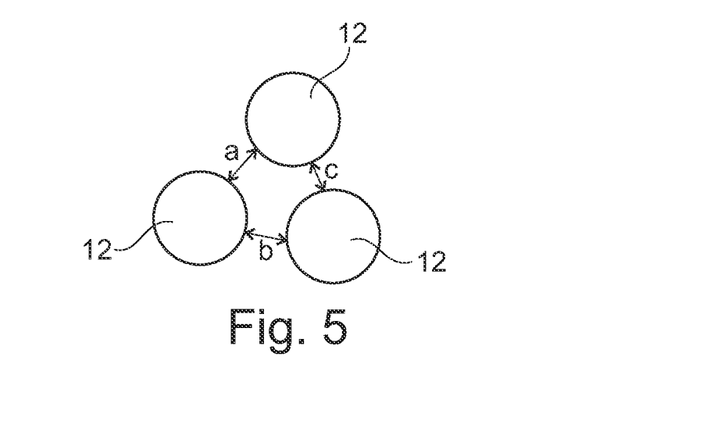
FIG. 5 shows schematically the measure of the distance between two fibers.

The mean-distance D or space between two adjacent fibers 12 on the applicator 10 measured at the root of the fibers 12, is preferably between 10 and 250 μm. The measure of the distance is shown in FIG. 5. Each fiber 12, shown in cross-section, has, in this measure, a round shape. The measured distance between two adjacent fibers 12 is the littlest distance, a, b, and c respectively in this example, as shown. The mean-distance D is calculated as the mean of all distances, i. e. D=Σd/n, with Σd being the sum of the individual distances and n being the number of fibers. In this example, Σd=a+b+c and n=3.

The assembly 5 may be offered to a user within a same packaging, for example a box, blister pack, case or sachet. In one variant, the applicator 10 and container 13 are offered separately to the consumer.

Figure 1:
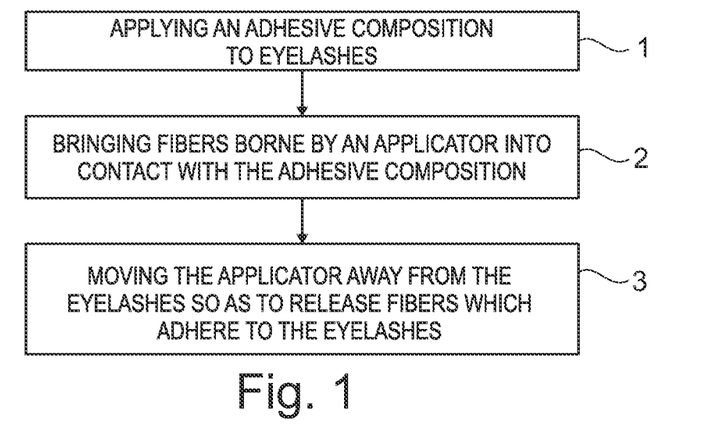
FIG. 1 is a block-diagram illustrating the successive steps of the method according to the invention.

The method according to the invention for adding fibers 12 to the natural eyelashes of a person has at least the following successive three steps, as shown in FIG. 1.

Figure 4A:
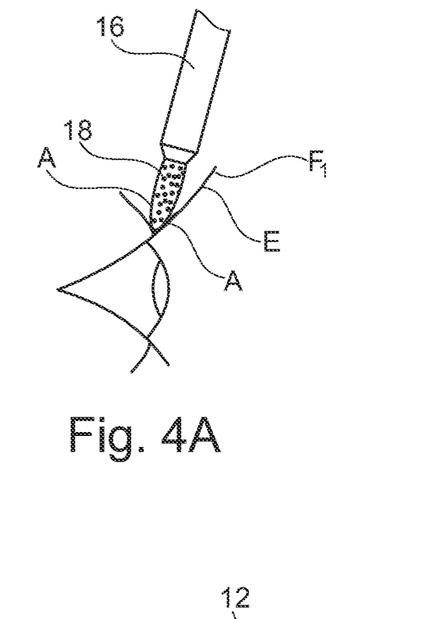
Figure 4B:
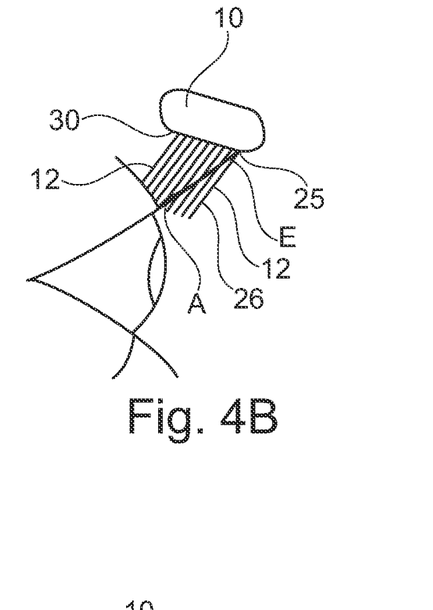

A first step 1 is implemented consisting in applying the adhesive composition A to at least part of eyelashes, preferably near the roots thereof. In one embodiment, only some of the eyelashes are concerned by the treatment, for example part of or all the eyelashes of the upper fringe. First step 1 is illustrated in FIG. 4A. The tip of the application element 18 loaded with the adhesive composition A comes into contact with the first millimeters of the top part of the upper fringe of eyelashes E on the roots thereof. The adhesive composition A is therefore applied only on the first millimeters of the eyelashes from the roots thereof, as shown in FIGS. 4A and 4B, for example on the first 4 mm of the eyelashes from the roots thereof.

In a second step 2, fibers 12 borne by the applicator 10 are brought into contact with the adhesive composition A. This second step 2 is illustrated in FIG. 4B. When the applicator 10 is brought into contact with the eyelashes coated with adhesive composition A, the second free ends 26 of fibers 12 come into contact with the adhesive composition A, as shown in FIG. 4B. The applicator 10 is arranged in order to make it possible to bring the fibers 12 into contact with the eyelashes E on which the adhesive composition A has been deposited.

The user handles the applicator 10 by the gripping portion 11 and put the second free ends 26 into contact with the adhesive composition A coating part of the eyelashes E. The applicator 10 is preferably approached by a substantially tangential movement, i.e. a razing gesture, illustrated by the arrow in FIG. 4B, until the fibers 12 are in contact with the adhesive composition A adhered to the eyelashes. This position may be maintained from several seconds to several minutes until some of the fibers 12 borne by the applicator 10 adhere to the eyelashes E.

Figure 4C:
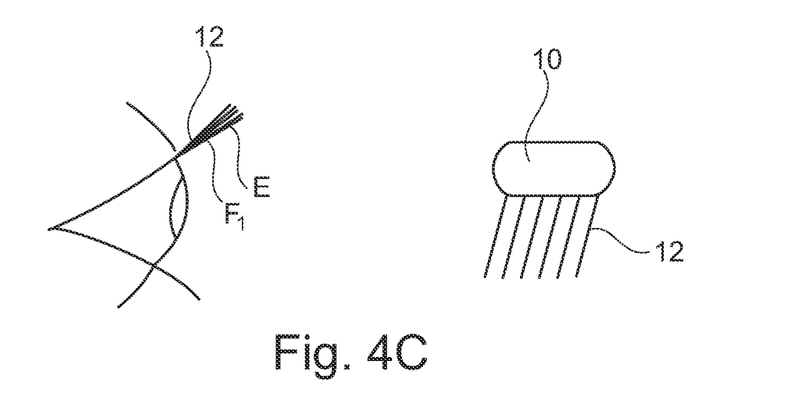

As the holding force for holding the fibers 12 on the applicator 10 is lower than the adhesive force for adhesion of the fibers to the adhesive composition A present on said eyelashes E, the user, by moving the applicator 10 away from the eyelashes in a third step 3, allows to release the fibers which adhere to the eyelashes. This third step 3 is illustrated by FIG. 4C. In this example, some fibers 12 remain on the support surface 30 of the applicator 10. Other fibers 12 adhere to the upper fringe F1 of the eyelashes E. As the adhesive composition A is only applied on the first millimeters of the eyelashes E from the roots, only part of the fibers 12, including the second end 26 thereof, adhere to the eyelashes.

It is to be noted that the method according to the invention may be at least partially implemented when the eye, whose eyelashes are treated, is closed.

Figure 3:
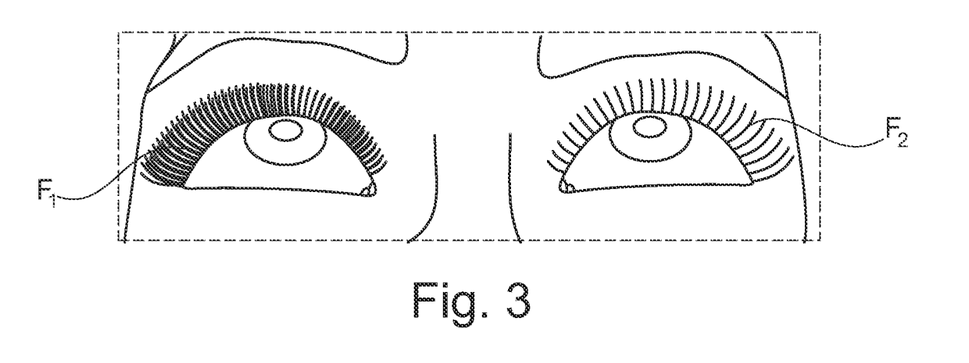
FIG. 3 is a photograph of the eyes and eyelashes of a person, one of the upper fringes of eyelashes being treated with the method according to the invention, FIGS. 4A, 4B and 4C schematically illustrate an eye of a person respectively during the implementation of three steps of the method shown in FIG. 1.

The result is shown in FIG. 3, wherein the upper fringe $F_1$ of eyelashes on the left is provided with additional fibers 12, whereas the other fringes of eyelashes, especially the upper fringe $F_2$ of eyelashes on the right, are not (comparative examples). The resulting effect looks very natural, as shown. Fibers 12 are positioned parallel to the eyelashes within the upper fringe $F_1$. The length of the fibers 12, after deposition on the eyelashes, is for example between 0.5 and 20 mm.

The invention is not limited to the shown embodiment.

In particular, as a variant, the container 13 containing the adhesive composition A may be any container such as a tube, a bottle, a pressurized receptacle, a coated support, a pump-dispenser bottle or pot, this list not being limited.

The fibers 12 may make an angle with the normal to the support surface 30, which may reach 45°.

The fibers may be retained in various ways on the applicator 10, for example with the aid of a mechanical system, for example a spring, which may change configuration in order to release the fibers.

Figure 6:
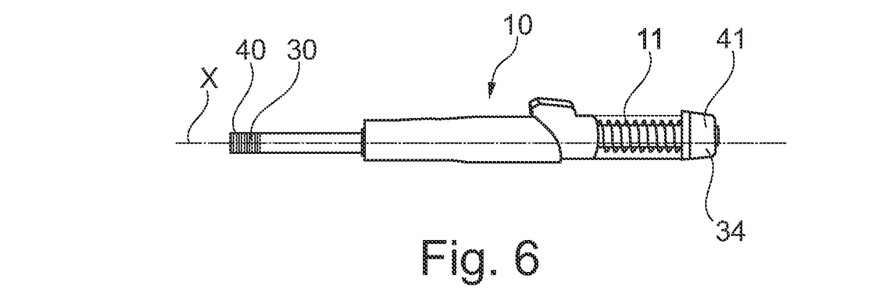
FIG. 6 represents schematically, in perspective and in side view, an example of an applicator for holding and releasing the fibers.
Figure 7:
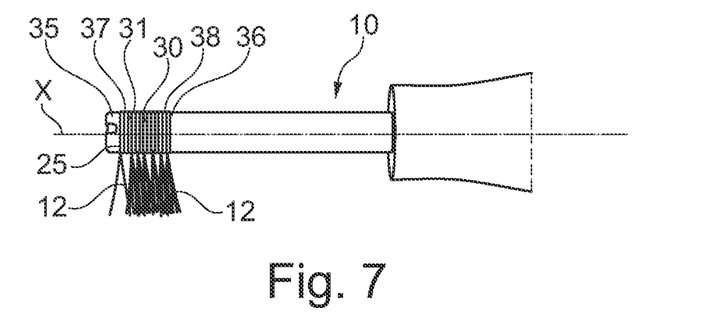
FIG. 7 shows partially and schematically, in perspective and in side view, the applicator of FIG. 6 holding fibers.
Figure 8:
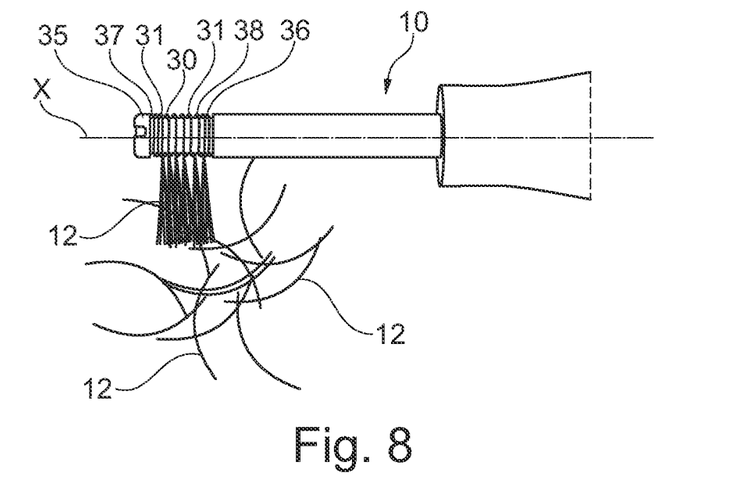
FIG. 8 shows partially and schematically, in perspective and in side view, the applicator of FIG. 6 releasing fibers.
Figure 9:
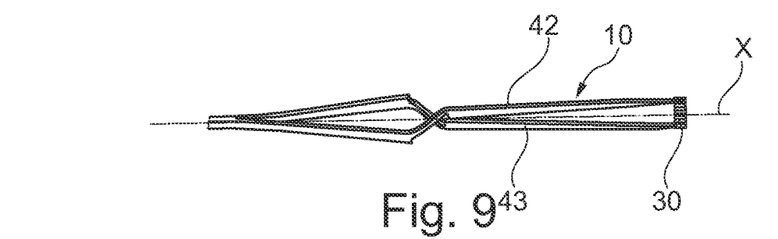
FIG. 9 represents schematically, in perspective and in side view, another example of an applicator for holding and releasing the fibers.
Figure 10:
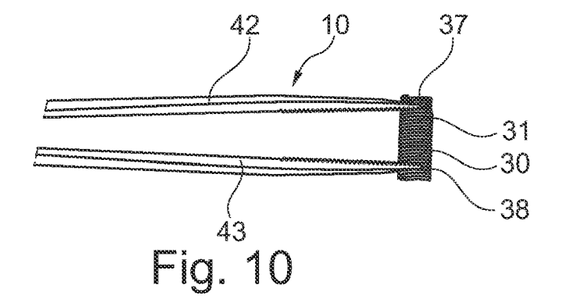
FIG. 10 shows partially and schematically, in perspective and in side view, the applicator of FIG. 9 in a holding position.
Figure 11:
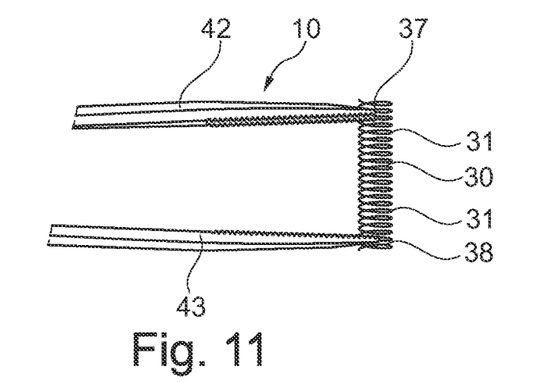
FIG. 11 shows partially and schematically, in perspective and in side view, the applicator of FIG. 9 in a releasing position.
Figure 12:
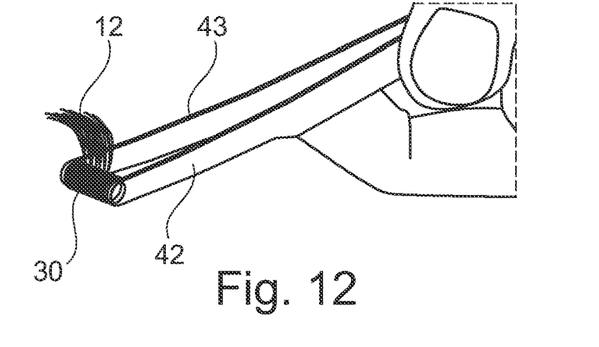
FIG. 12 shows partially and schematically, in perspective and in three-quarters view, the applicator of FIG. 9 holding fibers.

Such an applicator 10 is shown in FIGS. 6 to 8.

The applicator 10 has the shape of a pen in this example and comprises a spring 30 extending at an end 40 of the applicator 10 along the longitudinal axis X of the applicator 10. The spring 30 has two configurations, a retaining configuration shown in FIG. 7 and a releasing configuration shown in FIG. 8. In the retaining configuration, the fibers 12 are retained at their first end portions 25 between the coils 31 of the spring 30, the fibers 12 being locally substantially perpendicular to the longitudinal axis X of the spring 30. The spring 30 is operated manually by actuating a push button 34 at the other end 41 of the applicator 10 between the retaining and the releasing configurations. The applicator 10, in this example, has abutments 35 and 36 near both ends 37 and 38 of the spring 30, respectively, one abutment 35 being movable along the longitudinal axis X when actuating the push button 34, the other abutment 36 being immobile, i.e. fixed relative to a body of the applicator.

Another example of an applicator 10 has been represented in FIGS. 9 to 12.

In this example, the spring 30 is substantially perpendicular to the longitudinal axis X of the applicator 10. The spring 30 comprises two ends 37 and 38 that are attached to actuating levers 42 and 43, respectively, more precisely to the ends of the actuating levers 42 and 43. The actuating levers 42 and 43 are operated manually between the retaining configuration shown in FIG. 10 (without fibers) and in FIG. 12 (with fibers 12), and the releasing configuration shown in FIG. 11 (without fibers).

The invention is not limited to a particular system for retaining the fibers on the applicator 10, and rather than a spring, a system sensitive to a stimulus, such as a thermal or chemical stimulus, that makes it possible to modify the attachment force attaching the fibers to the applicator may be used. Use may for example also be made of an assembly of discs or lamellae that, when superposed and compressed, clamp the fibers.

The fibers may also be retained on the applicator by means of a material in which the fibers are implanted while the material is in the fluid state.

There may be fibers 12 of different colors retained by the applicator, in an organized or random manner, for application to a same fringe of eyelashes.

The invention claimed is:

1. A cosmetic treatment method for adding fibers to natural eyelashes, comprising:
   a) applying an adhesive composition to at least part of the eyelashes,
   b) providing an applicator on which a plurality of fibers are borne, the fibers of the plurality of fibers being substantially parallel to one another on the applicator, the fibers of the plurality of fibers, when borne by the applicator, being not linked to one another other than via the applicator,
   c) bringing said plurality of fibers borne by the applicator into contact with the eyelashes and with said adhesive composition present on said eyelashes, the fibers of the plurality of fibers being substantially parallel to the eyelashes when brought into contact with the eyelashes,
   d) moving the applicator away from the eyelashes, so as to release fibers which adhere to said eyelashes.

2. The method according to claim 1, wherein the adhesive composition is applied in step a) to said at least part of the eyelashes in a continuous or discontinuous manner.

3. The method according to claim 1, wherein the adhesive composition is applied in step a) on the eyelashes, from the roots of the eyelashes, over a length of the eyelashes ranging from about 0.1 mm to about 10 mm.

4. The method according to claim 1, wherein step c) is carried out by bringing fibers into contact with a top or lower part of an upper fringe of eyelashes.

5. The method according to claim 4, wherein step c) is carried out by bringing fibers into contact with the same part of the upper fringe of eyelashes, which was treated by the adhesive composition.

6. The method according to claim 4, wherein step c) is carried out by bringing fibers into contact with the top part of the upper fringe of eyelashes.

7. The method according to claim 1, wherein the applicator is brought close to the eyelashes in a tangential movement until the fibers contact the adhesive composition.

8. The method according to claim 1, wherein the fibers of the plurality of fibers are arranged as a bundle of fibers on the applicator.

9. An assembly for the cosmetic treatment of adding fibers to natural eyelashes, for the implementation of the method as defined in claim 1, comprising:
   an adhesive composition (A) to be applied to the eyelashes,
   an applicator retaining a plurality of releasable fibers, the applicator having a longitudinal axis, the applicator making it possible to bring the plurality of fibers into contact with the adhesive composition applied to the eyelashes to enable them to adhere to said composition and to release fibers, the fibers of the plurality of fibers, when borne by the applicator, being not linked to one another other than via the applicator,
   wherein
   the applicator comprises a mechanical system comprising one or more parts that can be moved relative to one another,
   the mechanical system is configured to pass from a fiber retaining configuration to a fiber releasing configuration.

10. The assembly according to claim 9, wherein the applicator retains a mixture of fibers that differ from one another in color.

11. The assembly according to claim 9, comprising an adhesive applicator for applying the adhesive composition to the eyelashes.

12. The assembly according to claim 11, the adhesive applicator comprising a flocked end piece.

13. The assembly according to claim 9, wherein the adhesive composition comprises or is constituted of an adhesive material chosen among pressure sensitive adhesives.

14. The assembly according to claim 9, wherein the adhesive composition comprises or is constituted of an adhesive material chosen among acrylic polymers or copolymers.

15. Assembly according to claim 9, wherein the adhesive composition is an acrylates/ethylhexyl acrylate copolymer.

16. An assembly for the cosmetic treatment of adding fibers to natural eyelashes, for the implementation of the method as defined in claim 1, comprising:
   an adhesive composition to be applied to the eyelashes,
   an adhesive applicator for applying the adhesive composition to the eyelashes comprising a flocked end piece,
   an applicator retaining a plurality of releasable fibers, the applicator having a longitudinal axis, the applicator making it possible to bring the plurality of releasable fibers into contact with the adhesive composition applied to the eyelashes to enable them to adhere to said composition and to release fibers,
   wherein
   the applicator comprises a mechanical system comprising one or more parts that can be moved relative to one another,
   the mechanical system being configured to pass from a fiber retaining configuration to a fiber releasing configuration, and
   the mechanical system comprises a spring that grips the fibers between its coils,
   wherein
   the spring comprises ends attached to actuating levers that are operated manually, and/or
   the spring is compressed or released along said longitudinal axis, the applicator having a push button and two abutments near both ends of the spring, one abutment being movable along the longitudinal axis when actuating the push button.

17. The assembly according to claim 16, wherein one abutment of the applicator is movable along the longitudinal axis when actuating the push button, the other abutment being immobile.

* * * * *